United States Patent [19]

Sapse

[11] 4,041,174

[45] Aug. 9, 1977

[54] METHOD OF TREATING DEPRESSION
[75] Inventor: Alfred T. Sapse, Beverly Hills, Calif.
[73] Assignee: Rom-Amer Pharmaceuticals, Ltd., Las Vegas, Nev.
[21] Appl. No.: 498,176
[22] Filed: Aug. 16, 1974
[51] Int. Cl.$^2$ .................................................. A61K 31/245
[52] U.S. Cl. .................................................. 424/310
[58] Field of Search .................................................. 424/310

Primary Examiner—Stanley J. Friedman
Attorney, Agent, or Firm—Sellers and Brace

[57] ABSTRACT

This invention is directed to treating depression in humans, especially older persons by (I) injection or infusion of local anesthetic, preferably in admixture with organic acid, sulfite salt, and acid salt, such as procaine hydrochloride, benzoic acid, dipotassium metabisulfite and disodium phosphate; during a period of at least three weeks at a dosage of at least 600 mg per week, or (II) by taking orally for a period of at least 30 days, at least about 300 mg daily. The treatment will be more intensive and/or more prolonged, dependent on the severity of the depression in the particular patient. A specific treating agent includes procaine hydrochloride, 0.1000 g; benzoic acid, 0.0060 g; dipotassium metabisulfite, 0.0050 gram; disodium phosphate, 0.0005 g; and either water to make five cc of solution or excipients to form a tablet (dragee) for oral ingestion.

22 Claims, No Drawings

METHOD OF TREATING DEPRESSION

BACKGROUND OF THE INVENTION

1. Field of the Invention

This invention relates to methods of treating mental depression in humans.

2. Description of the Prior Art

Depression is used herein in accordance with the usage of the Text: *The Medical Management of Depression*, by Sir Denis Hill and Leo E. Hollister (and others), Medcom Inc., 1970.

In 1957, Dr. Ana Aslan reported in the German Medical Journal *Therapiewoche*, 1, 10 (1957), her work with geriatric patients and the beneficial results obtained on manifestations of aging, such as, depression, arthritis, angina pectoris and hypertension by treatment with an aqueous solution of procaine hydrochloride, benzoic acid, dipotassium metabisulfite and disodium phosphate. Specifically the aqueous solution was referred to as Gerovital H3 (GH3) which on a 5 ml. vial basis contained, in addition to water, procaine hydrochloride, 0.1000 g; benzoic acid, 0.0060 g; dipotassium metabisulfite, 0.0050 g; and disodium phosphate, 0.0005 g; typically this solution has a pH of 3.3. Or the same amount of recited (named) ingredients were mixed with excipients to form tablets (dragees) which tablets are taken by oral ingestion. The tablets are referred to as Gerovital H3 tablets.

Dr. Aslan has reported in numerous publications since 1958 that the GH3 formulation gave better results than procaine hydrochloride alone.

In a paper entitled "Theoretical and Practical Aspects of Chemotherapeutic Techniques in the Retardation of Aging Processes" presented at the *Symposium on Theoretical Aspects of Aging*, February 7-8, 1974 Miami, Fla., Dr. Aslan reviewed not only her work but also the work of others since 1945, especially in depression. She pointed out that preventive treatment should begin at about age 45. She states that in all her work: "we use a one month series of 12 injections of 1 vial of Gerovital H3 of 5 ml."; [i.e., 100 mg of procaine hydrochloride per injection.] A 10-day drug free interval — pause or off-period— is taken between each series of 12 injections.

The recommended treatment for tablets is: two tablets daily during 12 days (24 tablets in all); then a pause or off-period of 18 or 30 days before the next series of 12 days on tablets. [Gerovital H3, Chimimport, Bucharest, Romania.]

Allergic reactions to GH3 occur in about 1 out of 6,000 cases (Aslan, ibid). A test for allergy using GH3 solution: The first day one ml of GH3 solution is introduced by subcutaneous injection, and on the second day two ml are injected intramuscularly. If no allergic phenomena are recorded, the treatment may be started. A test for allergy using tablets: the first 2 days, only one tablet is taken; if no allergic phenomena are recorded the treatment may be started. [Gerovital H3, ibid.]

SUMMARY OF THE INVENTION

The invention is directed to a method of treating depression, preferably the depressed patient has an age of at least about 45 years, which method consists essentially of treating a depressed patient with, (I) by injection or infusion, during a period of at least 3 weeks with at least 600 mg a week, or (II) at least about 300 mg daily, taken orally, for a period of at least 30 days, of (i) a local anesthetic which is a specific depressant of sensory nerves and may be administered by injection, infusion, or orally; or (ii) metabolic splinters of such a local anesthetic.

The local anesthetic may be selected from the class consisting of alcohols, alkyl ethers, amines, aminoalcohols, amino alkyl ethers, amino ketones, carboxylic acid esters, carboxylic amides, carbamic acid esters, amidines and guanidines. Desirably said anesthetic is carboxylic acid ester, such as procaine, including an acid salt thereof, or carboxylic acid amide, such as lidocaine.

Beneficial results are obtained by having present along with the defined anesthetic an organic weak acid; desirably there is also present a sulfite salt; furthermore, there may also be present an acid salt such as is used for buffering purposes.

As especially preferred formulation of local anesthetic consists essentially of procaine hydrochloride, benzoic acid, dipotassium metabisulfite, and disodium phosphate. And particularly wherein the relative weight proportions of the recited ingredients are: procaine hydrochloride, 0.1000 g; benzoic, acid, 0.0060 g; dipotassium metabisulfite, 0.0050 g; and disodium phosphate, 0.0005 g. In one preferred embodiment the recited amounts of ingredients are dissolved in water to make 5 ml of solution. In another preferred embodiment, the recited amounts of ingredients are admixed with excipients to form a tablet containing the same amout of active materials as one five ml vial of solution.

Another method of treating depression consisting essentially of treating a depressed patient with, (i) a local anesthetic which is a specific depressant of sensory nerves and may be administered by injection, infusion, or orally; or (ii) metabolic splinters of such a local anesthetic; or a regimen (I) of about four weeks, of from about 600 mg per week to less than a toxic amount on a daily basis, by injection or infusion, or (II) about 300–900 mg daily, taken orally, for at least about 4 weeks. The desirarable maximum daily dosage by injection or infusion is less than 1,000 mg. Preferably the maximum daily dosage by injection or infusion is not more than 500 mg. The above method may include in regimen (I) a first week adjustment period wherein the treatment level is not more than 300 mg distributed over that first week.

An especially prefered regimen by injection or infusion for a mildly depressed patient consists essentially of (a) a first four week treatment period, as defined in "another method above"; (b) an off-period of about two weeks; and (c) a second four week treatment period, as defined in "another method above"; and for a more severly depressed patient additional course or courses consisting of a four week treatment period, as defined in "another method above", and a two week off-period are added to aforesaid treatment. For example a moderately depressed patient would be given one more course of treatment; a severly depressed patient would be given two or more additional courses of treatment. As the patient may require, each 4 week treatment course may begin with a one week adjustment treatment level of not more than 300 mg distributed over that first week.

Finally when the treatment has progressed to that point, the treated depressed patient is placed on a maintenance program having about four week treatment periods, by injection or infusion, according to regimen (I) aforesaid and having about 4–6 week off-periods.

An especially preferred regimen by oral ingestion consists essentially of, for a mildly depressed patient, (a) a first treatment period of about 30–42 days, as defined in "another method above"; (b) an off-period of about 14 days; (c) a second treatment period of about 30–42 days, as defined in "another method above"; and for a more severely depressed patient additional course or courses consisting of an about 30–42 day treatment period, as defined hereinbefore, and another about 14 day off-period are added to the treatment regimen. For example, a moderately depressed patient would be given one more course of treatment; a severely depressed patient would be given two or more courses of treatment.

Finally when the treatment has progressed to that point, the treated depressed patient is placed on a maintenance program having about 30–42 day oral ingestion periods according to regimen (II) as defined in "another method above", and having off-period of about 4–8 weeks.

A particular method of treating depression in a patient having an age of at least 45 years, which method consists essentially of: (1) injecting or infusing said patient with three 100 mg portions of aqueous solution, defined as GH3, distributed over the first week of said treatment; and (2) injecting or infusing said patient in each of the second, third, and fourth weeks of said treatment with 600 mg of the aqueous solution defined as GH3, distributed over each of said weeks; desirably the 600 mg is given as three 200 mg doses.

DESCRIPTION OF THE INVENTION AND EXAMPLES

EXAMPLE A

The purpose of this study was to evaluate the therapeutic efficacy and safety of aqueous GH3 in the treatment of depressive disorders in the aged, by comparing it in a double-blind study with imipramine and placebo in an outpatient population.

GH3 as used in this study consisted of 5 cc ampules each containing procaine hydrochloride, 0.1000 g; benzoic acid, 0.0060 g; dipotassium metabisulfite, 0.0050 g; disodium phosphate, 0.0005 g; and water to make 5 cc. This GH3 was manufactured in Romania.

In order to retain the double-blind aspect of this study, the test preparations were made as follows:

1. GH3 supplied in 5 cc ampules.
2. Placebo in the form of normal saline in matching ampules.
3. Imipramine supplied in a capsule each containing 25 mg.
4. Placebo capsules to match the imipramine capsules.

The patients were 60 years old and over, with no upper limit as to age, no restriction as to sex, and had depressive disorders of at least mild in global severity. This was determined by using a Clinical Global Impression (CGI) scale of 1 to 7 where 3 indicates mild illness.

In this study, a despressive disorder is operationally defined as manifesting: 1. A mood disturbance which is characterized by pervasive feelings and complaints of being depressed, sad, and tearful. 2. Physiological symptoms which include diurnal variation, disturbance of sleep, decreased appetite, decreased weight, decreased libido, constipation, tachycardia, and unexplainable fatigue. 3. Psychomotor disturbances which are either that of retardation or agitation. 4. Psychological disturbances which include confusion, emptiness, hopelessness, indecisiveness, irritability, dissatisfaction, personal devaluation, and suicidal rumination.

The following were excluded from the study: 1. Actively suicidal patients. 2. Patients who were incapable of spontaneous conversation and activity. 3. Patients who were severely demented. 4. Patients who were schizophrenic, or had evidences of a thought disorder. 5. Patients who were on the following medications: sulfonamides, neostigmine or physostigmine.

All patients were free of all psychotropic drugs for at least seven days prior to entry to the study protocol.

This was a double-blind study of 4 weeks in duration. All patients received intramuscular medication using the following schedule: Week 1: 5 cc, 3 times a week. Weeks 2,3 and 4: Ten cc (two 5cc ampules), 3 times a week.

All patients received oral ingestion medication using the following schedule: Weeks 1 and 2: Day 1- one capsule at bedtime; day 2 - one capsule, twice a day; days 3-14 - one capsule three times a day. Durings weeks 3 and 4, the oral dosage could be increased to no more than 2 capsules, three times a day, or decreased in accordance with the investigator's clinical judgment of the the patient's clinical course.

Patients were evaluated psychiatrically and given a diagnosis and a Clinical Global Impression (CGI) rating of their illness on Day Zero. Patients were interviewed by a second psychiatrists who completed the Depression Status Inventory (DSI), and the Anxiety Status Inventory (ASI). All patients completed the Self-rating Depression Scale (SDS), and the Self-rating Anxiety Scale (SAS). All of these were repeated on Day 28.

In addition, appropriate examinations were performed before and after the test trial (physical examination, blood chemistries, blood counts, uninalysis, and EKG).

A total of 36 patients were studied; 6 patients dropped out of the study. Of the 30 patients who completed the study, 9 received GH3, 11 received imipramine and 10 received placebo. The ages of the patients in the GH3 group ranged from 61 to 77 years (mean = 67.2). The ages of the patients in the imipramine group ranged from 60 to 79 (mean = 68.5) The ages of the placebo group ranged from 63 to 74 = (mean = 68.7).

The actual dosage of patients on GH3 during the 4-week period of treatment showed a mean total dosage of 2,022 mg, with a range of 1,500 to 2,100 mg/total dosage.

The actual dosage of patients on imipramine during Week 1 showed a mean of 80.8 mg/day with a range of 64.3 to 96.5 mg. During Weeks 2–4, the mean dosage was 72.2 mg/day with a range of 35.8 to 117.8 mg/day.

Statistical analysis using the $t$-test of significance were performed, all two-tailed (2° of freedom), and the $t$ statistic corrected when multiple $t$ tests were done using the Bonferroni tables.

For the GH3 tested Group: in comparing Day 0 with Day 28 the results indicated that the patients improved signicantly on CGI, DSI, SDS, ASI, and SAS, with all $p$ values (probability values) less than 0.05. This demonstrates that GH3 was efficacious in the treatment of this group of depressed patients.

For the imipramine tested Group: In comparing Day 0 with Day 28, these patients improved significantly on all variables except the SAS, with $p$ values of less than 0.05.

For the Placebo Group: In comparing Day 0 with Day 28, these patients showed no significant changes in any of the variables measured.

There were six drop-outs in the study; of these three patients became clinically worse during the first week of the drug trail. All three patients became anxious and agitated and required hospitalization. One patient dropped out because of an unrelated medical illness. Two patients dropped out because of lack of interest in continuing the study.

The results of this double-blind study comparing Gerovital H3 versus imipramine and placebo showed that by comparing pre- and post-treatment scores on several rating scales measuring depression, both Gerovital H3 and imipramine treated patients improved significantly with respect to their depressive disorders, while placebo treated patients did not. Further, the results of this study showed that using the clinical global impression and the Zung selfdepression scale, the change scores obtained from calculating pre-treatment to post-treatment differences showed Gerovital H3 to be superior to imipramine since the differences between Gerovital H3 and placebo were significantly different, while the differences between imipramine and placebo were not significantly different.

In addition to being an efficacious drug in the treatment of depression in the elderly, Gerovital H3 seems to have some additional advantages in terms of its pharmacological effects and increased safety.

EXAMPLE B

The purpose of this study was to evaluate the therapeutic efficacy and safety of Gerovital H3 (GH3) in the treatment of depressive disorders in a private practice population. This was a double-blind study using a solution of GH3, as described in Example A, administered intramuscularly.

Suitable for consideration for participating in this study were patients 45 years old or older, men and women, who had depressive disorders of at least mild severity. This was determined by using a Clinical Global Impression (CGI) scale of 1 to 7 with 3 indicating mild depression.

Patients were excluded from this study for the same reasons listed in Example A and were free of psychotropic drugs before entering the study.

Gerovital H3 was supplied in 5 cc ampules, as described in Example A, and placebo in the form of normal saline was supplied in matching ampules.

This was a double blind study of four weeks duration. All patients received intramuscular injections using the following schedule: Week 1 - 5 cc, 3 times a week; Weeks 2, 3, and 4 - 10 cc (2 five cc ampules), 3 times a week. (this is equivalent to a total dosage of 2100 mg of procaine hydrochloride.)

Of the 64 patients who entered the study, 1 dropped out. Of the 63 patients who completed the study, 33 received GH3 and 30 received placebo.

In the GH3 group of 22 women and 11 men, the ages ranged from 45 to 81 (mean = 58.5). In the Placebo group of 10 women and 20 men, the ages ranged from 45 to 83 (mean = 58.9).

All patients received the scheduled dosage of 21 five cc injections.

Patients were evaluated psychiatrically and given a diagnosis and a CGI of the severity of illness pre-treatment. Patients were also evaluated for depressive disorder using the Hamilton Rating Scale for Depression (HRD) and the Zung Self-rating Depression Scale (SDS). These ratings were repeated at the end of the treatment period. In addition, appropriate examinations were performed before and after test trails (physical examination, blood chemistries, blood counts, and urinalysis).

Statistical analyses using the $t$-test, two-tailed were performed on the three variables measured (CGI, HRD, AND SDS) for within group comparison (pre-treatment versus post-treatment), and for between group comparisons (GH3 versus placebo).

The CGI scores for the two groups are not significantly different from each other at pre-treatment evaluation. At the end of the treatment, the GH3 group had improved significantly over the Placebo group with $p$ = less than 0.01.

The HRD scores of the two groups are not significantly different at pre-treatment evaluation.. At the end of the treatment the GH3 group improved significantly over the Placebo group with $p$ = less than 0.01.

The SDS scores for the two groups are comparable and not significantly different from each other. At the end of the treatment period, the GH3 group showed greater improvement which was significantly different with $p$ = less than 0.05.

There is a significant correlation between the CGI, HRD, and SDS scores at pre-treatment and post-treatment evaluations.

This study concludes from the data presented that Gerovital H3 is an efficacious drug in the treatment of depressive disorders in an adult population, and that it is also a safe drug.

EXAMPLE C

The purpose of this study was, with an open design, to investigate the antidepressive activity of Gerovital H3 in senilearteriosclerotic patients, as well as to investigate a dose range for this drug.

Ten geriatric patients, aged 63 to 82 years, were selected for this study; all of the patients had histories exceeding two years and most of the patients manifested symptoms of disorientation, memory impairment, paranoid ideation, agitation, ward management problems, withdrawal, and features of depression, including pessimism in general, lack of interest, helplessness, hopelessness, suicidal ideation, insomnia, somatic preoccupation, anorexia, etc.

This was an open study, which fell into three stages: a baseline (placebo) period of at least 1 week; a stage of active drug treatment extending over a 3 week period; and a post-medication placebo period of at least 2 weeks.

At the end of the baseline period, and thereafter weekly, patients were rated on the Hamilton Depression Scale and the Clinical Global Impressions Scale by one psychiatrist, and on the Nurses Observation Scale for Inpatient Evaluation by the nursing staff.

It was decided to commence treatment with 100 mg intramuscularly of the drug, 3 times a week for the first week, and, in the absence of response, to raise the dose to 150 mg in the second week and to 200 mg in the third week.

No clinical changes were observed before the end of the second week of active treatment, by which time most of the patients were on the 150 mg dosage. In fact, a further increase to 200 mg was necessary in the majority of cases, 6 out of 10; it was at the end of the third week that mean changes as recorded on the Hamilton Scale became statistically significant.

Somatization and Anxiety/Depression were the only area in which statistically significant changes were observed.

Further, since no side effects were observed at any stage of the study, the drug must be regarded as being quite safe in this dose range.

EXAMPLE D

This study was designed to assess levels of procaine in the urine and blood of dogs (beagles) which had been given Gerovital H3 in tablet form, 100 mg procaine hydrochloride per tablet.

Six adult beagles were used in the test; each dog received a single oral dose of 2 GH3 tablets. Total urine was collected for 24 hours and divided in 0–8 hour portions and 8–24 hour portions. Blood sample were taken over 8 hours.

Procaine was definitely found in the blood plasma.

Definite identification of procaine and para aminobenzoic acid (PABA) in the urine of each dog during the 0–8 hour portion and definite identification of PABA in the 8–24 hour portion.

The presence of procaine and PABA in the dog urine confirms that discrete non-hydrolyzed procaine had been in the blood stream of the dog.

A single beagle received 200 mg of solid procaine hydrochloride USP, orally. "Attempts to identify procaine after administration of procaine hydrochloride failed, indicating its rapid disappearance from the peripheral blood."

EXAMPLE E

This study was made with human patients who received 100 mg tablets of Gerovital H3; simultaneously other patients received IM injections of 100 mg ampules of aqueous Gerovital H3; urine samples were drawn and analyzed for procaine and PABA.

The comparative results establish that oral administration of Gerovital H3 results in procaine being absorbed intact and excreted into the urine intact. However, on the basis of this series of tests, it is established that the bioavailability of procaine taken orally is far less than that taken by injection; on a single dosage basis, 600 mg orally may be about equivalent to 100 mg taken intramuscularly.

This difference in bioavailability is taken into account in the regimens utilized by patients on injection treatment versus patients on oral, tablet, treatment.

The foregoing data establish conclusively that the standard regimen published by Dr. Ana Aslan is relatively ineffective for treatment of depression and that a much more severe treatment is necessary to obtain beneficial results.

In the case of the "adjustment week", it has been observed that the dosage sould not be more than 300 mg for the week; the 300 mg must be distributed over the week, such as 100 mg a day for three days; or 50 mg a day for 6 days. Some patients require the first adjustment week to be given with each course; others can do without the adjustment week at all, or after the first course of treatment.

In the case of the treatment courses, the dosage by injection or infusion can be given all in one day of the particular week —provided that dose is less than the toxic daily amount— or it may be spaced (distributed) over the week; for example, one injection of 200 mg each day for a total of three days during a 600 mg a week regimen.

The preferred mode of injection is intramuscular (IM).

Also in the case of injection treatment, it has been observed that the earliest appearance of beneficial results comes in the third week of treatment.

Off-periods (pauses) are necessary; the why is not known.

Bioavailability studies have shown that enormously more of the local anesthetic, specifically procaine hydrochloride, must be ingested in order to obtain equivalent beneficial results shown by the 200 mg, for instance, taken by injection IM.

Throughout this application, the dosage has been referred to as so many mg (milligrams) of the local anesthetic per se. It is to be understood that the numbers are strictly applicable to procaine hydrochloride; other species may deviated from the given dosages but not significantly. In any case, the physician will adjust the dosage to suit the particular patient and this will automatically eliminate and deviation in "strength" among the various local anesthetics which can be used in this invention.

It is to be understood that each depressed patient will be be under the care of a physician while undergoing treatment and items of procedure and dosage may be changed to suit the needs of the particular patient without violating the concept and intent of the described invention.

DESCRIPTION OF THE TREATING AGENT

The treating agent utilized in the invention is selected from the class consisting of (i) a local anesthetic which is a specific depressant of sensory nerves and may be administered by injection, infusion, or orally, and is sufficiently water soluble to permit formation of an injectable aqueous solution; and (ii) metabolic splinters of such a local anesthetic. The anesthetic may include other substances, such as, organic weak acid, sulfite salt, and acid salt. More commonly the agent is used in the form of an aqueous solution.

THE LOCAL ANESTHETIC COMPONENT

The local anesthetic may be in the form of the compound itself; or in the form of a hydrate; or in the form of an acid salt or complex; or in chemical combination which will slowly release the active material. To illustrate: procaine base; procaine dihydrate; procaine hydrochloride; procaine-glucose; and procaine-thiamine.

Certain chemical sub-classes of local anesthetics are of particular interest:

1. Alcohols, such as, chlorobutanol, benzyl alcohol, and saligenin.
2. Alkyl ethers, such as, pistocaine.
3. Amines, such as, N-phenylmethyl(4-diethylamino)N'-phenymethylenemthyl amine and 1-(diethylamino)-2-quinolyl ethane.
4. Aminoalcohols, such as, 3-amino-6-methyl heptan-4-ol; 1-phenyl-2-methyl-(methylamino) ethan-1-ol; 1-phenyl-2-methyl(methyltolylamino) ethan-1-ol.
5. Amino alkyl ethers, such as, pramoxine and dimethisoquin.
6. Aminoketones, such as, dyclonine and falicaine.
7. Carboxylic acid esters, such as, benzocaine, butyl aminobenzoate, procaine base, procaine dihydrate, procaine nitrate, procaine butyrate, procane borate, procaine hydrochloride, 2-chloroprocaine hydrochloride, butethamine formate, butethamine hydrochloride, metabutethamine hydrochloride, tetracaine hydrochloride, tutocaine hydrochloride, propanocaine, propoxycaine hyrochloride, metabutoxycaine hydrochloride, meprylcaine, meprylcaine hydrochloride, isobucaine hydrochloride, naepaine, butacaine, benoxinate, proparacaine, cyclomethycaine, hexylcaine hydrochloride, piperocaine hyrdrochloride, amydricaine, amydricaine hydrochloride, amydricaine nitrate, parethoxycaine, parethoxycaine hydrochloride, mepivacaine, and mepivacaine hydrochloride.

8. Carboxylic Acid Amides, such as, lidocaine, lidocaine hydrochloride, prilocaine hydrochloride, pyrrocaine hyrochloride, butanilicaine hydrochloride, butanilicaine phosphate and dibucaine hydrochloride.

9. Carbamic acid esters, such as, diperodon.

10. Amidines, such as, phenacaine.

11. Guanidines, such as, guanicaine.

The aforesaid non-limiting illustrative listed compounds are identified by their common names. Generic names and structural formulas are given in : (1) International Encyclopedia of Pharmacology and Therapeutics, Volume 1, Section 8, "Local Anesthetics" Chapter 2, Pergamon Press, New York, 1971. (2) Remington's Pharmaceutical Sciences, 14th Edition, Chapter 59, "Local Anesthetics" Mack Publishing Company, 1970. (3) The Merck Index, Eighth Edition, Merck & Co., 1968.

CARBOXYLIC ACID ESTERS

A desired subclass of the defined focal anesthetics is the carboxylic acid esters. The acid portion may be aromatic: monocyclic (benzenoid), fused dicyclic (derviced from naphthalene, pentalene, indene, etc.), bicyclic ring assembly (derived from biphenyl, binaphthalene, etc) with the ring(s) substituted, if any, by one or more aliphatic hydrocarbon groups, halogens, hydroxy groups (OH), amino groups (NH$_2$ or NHR' or NR'R''), carboxyl group(s) of course, and other groups which do not interfere with the lpharmacological effectivenss of the ester. Or the acid portion may bederived from aliphatic radicals having at least 3 carbon atoms; or cycloaliphatic radicals; or arylaliphatic radicals; or heterocyclic, such as N-heterocyclic.

The alcohol portion is aliphatic in character and may be substituted by aryl groups, heterocyclic groups, halogen, hydroxy (unreacted) groups, and other groups which do not interfere with the pharmaceutical action of the ester. Especially preferred alcohols have a substitutent amino group with one or both of the amino hydrogens replaced by alkyl, aryl, alkoxy, oxyalkyl, cycloalkyl, heterocyclic groups, or the amino N may form part of a heterocyclic ring.

The water solubility of the particular ester may not be sufficient for the purposes of, or a particular embodiment of, the invention. The ester can be reacted to form a hydrate; or can be reacted with an acid to form a salt or complex; thereby producing a more water soluble pharamcologically effective compound. It is to be understood that the particular acid used will be consonant with the intended pharmaceutical use of the salt. Some illustrative organic and inorganic acids are: hydrochloride, sulfuric, nitric, phosphoric, boron, formic, acetic, and butyric.

A preferred subclass of aromatic monocarboxylic acid ester local anesthetics is shown by the following (I) general structural formula:

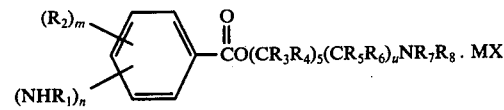

where in said formula (I), n is a integer equal to 0-2;

m is a integer equal to 0-4;

n + m is not more than 5;

R$_1$ is H or alkyl having 1-5 carbon atoms;

R$_2$ is halogen, hydroxy, alkoxy, alkyl, aryl, or cycloakyl and alkoxy and alkyl each have 1-5 carbon atoms;

R$_3$, R$_4$, R$_5$, and R$_6$, respectively, are H, alkyl, alkylene, aryl, or cycloalkyl and alkyl and alkylene each have 1-5 carbon atoms;

R$_7$ and R$_8$, respectively, are H, alkyl having 1-5 carbon atoms, aryl, cycloalkyl, alkoxy, oxyalkyl, heterocyclic, and only one of R$_7$ and R$_8$ may be H;

NR$_7$R$_8$ may be N-heterocyclic;

s and u, respectively, are 0-5 and at least one of s and u must be greater than zero; and MX is hydrate, acid moiety, or may not exist, i.e., is "zero".

CARBOXYLIC ACID AMIDES

Another desired subclass of the defined local anesthetics is the carboxylic acid amides. The "amide portion" and the ∓alcohol portion" of the anesthetic compound may be selected from any of the illustrative groups set forth under aforesaid "Carboxylic Acid Esters" Section.

Formula I, supra is adopted in part to define a preferred subclass of aromatic monocarboxylic acid amides (II) where

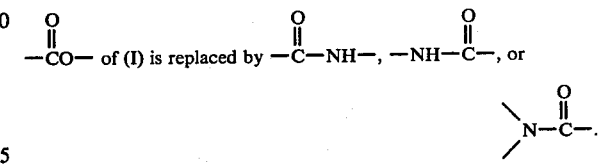

ESTERS AND AMIDES

International Encyclopedia, Volume 1, Local Anesthetics, ibid, page 47, Table 2, illustrates the herein preferred esters and amides in terms of 'lipophili', 'hydrophilic', and 'intermediate ' chemical structural elements. This material is incorporated by reference hereinto.

METABOLIC SPLINTER COMPONENT

The treating agent may contain as active ingredient compound(s) known as metabolic splinters (metabolites) from the breakdown of a local anesthetic within an in vivo system. Or the treating agent may contain a mixture of local anesthetic and metabolite. For example, it is known that procaine hydrolyses to p-aminobenzoic acid (PABA) and diethylaminoethanol (DEAE); each of these metabolites performs a useful pharmacological function in the system. A metabolite may perform a dual role in the treating agent by acting both as a metabolic splinter active ingredient and as an organic weak acid, such as, p-aminobenzoic acid.

ORGANIC WEAK ACID COMPONENT

In addition to the defined local anesthetic and/or metabolite, the treating agent may include an organic weak acid. This organic weak acid may be any one which does not interfere with the intended use of the anesthetic and is sufficiently water soluble to permit formation of reasonable sized doses. The organic weak acids may be simple organic carboxylic acids containing one or more carboxylic (COOH) groups; or may be multifunctional compounds such as, amino acids, hydroxy acids, amino aromatic carboxylic acids, or the vitamin acids, such as, retinoic (vitamin A acid), nicotinic acid (niacin), pantothetic acid, pteroylglytamic acid (folic), and ascorbic acid (vitamin C acid); or the lower alkanoic acid derivatives of ethylene diamine, propylene diamine and their homologues, such as diethylene triamine and dipropylene triamine.

The aryl monocarboxylic acids, such as, benzoic acid having one or more substituents which do not interfere with the active ingredient, are a preferred class of organic weak acids. Illustrative are benzoic acid, toluic acid, hydroxybenzoic acid, chlorobenzoic acid, aminobenzoic acid, phenylacetic acid, phenylpropenoic acid, and methoxybenzoic acid.

Lange's Handbook of Chemistry, 11th Edition, McGraw-Hill Book Company, 1973, in Section 5 provides pK values in aqueous solution of an extensive list of organic compounds. pK is the symbol of the logarithm of the reciprocal of the dissociation constant of an electrolyte: $pK = \log(1/K)$. A pK on the order of 1.5 desirably larger, is suitable. $pK = 2$ corresponds roughly to $K = 10^{-3}$. To illustrate: p-Aminobenzoic acid has a $pK = 2.38$; this converts to $K = b\ 4.2 \times 10^{-3}$. The pK values of some organic weak acids of interest are set out in Table 1.

Table 1

| Organic Weak Acid | pK |
|---|---|
| Acetic | 4.76 |
| Aminoacetic (glycine) | 2.35 |
| p-Aminobenzoic | 2.38 |
| 5-Aminosalicylic | 2.74 |
| Benzoic | 4.21 |
| p-Chlorobenzoic | 3.99 |
| Dichloroacetic | 1.3 |
| Citric | 3.13 ($pK_1$) |
| o-Hydroxybenzoic (salicylic) | 3.0 |
| p-Methoxybenzoic (anisic) | 4.49 |
| 1-Naphthoic | 3.70 |
| Phenylacetic | 4.31 |
| Phenylpropenoic (cinnamic) | 4.44 |
| p-Toluic | 4.37 |
| Ethylenediaminetetraacetic | 6.27 ($pK_1$) |
| Diethylenetriaminepentaacetic | 1.80 ($pK_1$) |
|  | 2.55 ($pK_2$) |
| Dimethylethylenediaminediacetic | 6.63 ($pK_1$) |

SULFITE SALT COMPONENT

The effectivenss of the defined local anesthetic is improved by the presence of a sulfite salt, especially by the potassium form. The sulfite salt includes the pharmacologically acceptable salts of sulfite ($SO_3$); bisulfite (hydrogen sulfite, $HSO_3$); metabisulfite (pyrosulfite, $S_2O_5$); thiosulfate ($S_2O_3$); and hyrosulfite (dethionite, $S_2O_4$). The alkali metal salts are preferred and the potassium salts especially preferred, such as, potassium metabisulfite.

ACID SALT COMPONENT

It is known that the aromatic carboxylic esters are rapidly hydrolysed at pH near neutral. It is very desirable that aqueous solutions of the defined local anesthetics have a pH on the acid side. To assist in maintaining such a pH, an acid salt component is desirably present in the aqueous solution of local anesthetic. Any of the acid salts conventionally used as buffer salts, such as, acetates, borates, phthalates and phosphates are suitable. However, most acid salts of low dissociation constant which salts are pharmacologically acceptable by the organism can be used as acid salt component. A preferred salt is the potassium or sodium acid phosphate, such as, disodium phosphate.

AQUEOUS SOLUTIONS

For injection or infusion the treating agent is placed into aqueous solution. Sufficient water is present to dissolve the components and to provide a low viscosity solution that is readily injectable or infusible.

The treating agent may consist only of the defined local anesthetic and/or metabolite and water. Usually beneficial results are obtained when the agent includes local anesthetic and organic weak acid. The relative amounts of the defined anesthetic and organic weak acid will vary with the particular combination of components. Some "minor testing" may be necessary to obtain a specific aqueous solution having the desired 'lasting property' such as is evident in procaine hydrochloride and benzoic acid solutions.

Benefits are obtained by the presence of the defined sulfite salt along with the defined local anesthetic, especially the potassium salt. The Sulfite salt may be present along with the defined local anesthetic alone or in combination with the defined organic weak acid or in combination with the defined acid salt, or any combination of these components.

The carboxylic acid ester local anesthetics are particularly benefited by the inclusion of organic weak acid and/or sulfite salt and/or acid salt. A treating agent including all four of these defined component is preferred.

A preferred embodiment of aqueous solution consists essentially of procaine hydrochloride, benzoic acid, dipotassium metabisulfate, and disodium phosphate.

A commercially available specific embodiment of this solution consists of a five (5) cc aqueous solution containing procaine hydrochloride, 0.1000 gram; benzoic acid, 0.0060 gram; dipotassium metabisulfite, 0.0050 gram; and disodium phosphate, 0.0005 gram. This specific embodiment is sold as Gerovital H3 by Rom-Amer Pharmaceuticals Ltd.

TABLET AND CAPSULE COMPOSITION

The defined treating agent may be taken orally, for example drinking a suitable solution. However, it is more convenient to place the active ingredient, plus one or more or all of the other defined possible components, into a capsule or into a tablet and to ingest the capsule or tablet in order to introduce the agent into the body.

Usually the formation a tablet requires that diluents and binders — excipients — be admixed with the agent component(s); the mixture of agent and excipents is then molded or compressed into the proper sized tablet. The tablet may or may not be sugar coated to mask the taste of the 'active' ingredients.

A commercially available tablet (Gerovital H3 from Rom-Amer Pharmaceuticals Ltd) has the following composition, Table 2.

Table 2

| 'Active' Component | Gram |
|---|---|
| Procaine Hydrochloride | 0.1000 |
| Benzoic acid | 0.0060 |
| Potassium metabisulfite | 0.0050 |
| Disodium phosphate | 0.0005 |
| Excipients for Compression and Coating | |
| Lactose | 0.0200 |
| Cornstarch | 0.1008 |
| Gelatin | 0.00378 |
| Stearin | 0.0050 |
| Sugar | 0.16072 |
| Talc | 0.0776 |
| Yellow wax | 0.0004 |
| Carnauba wax | 0.0002 |
| Total | 0.48000 |

Thus having described the invention, what is claimed is:

1. A method of treating depression which method consists essentially of treating a depressed patient with,
   I. by injection or infusion, during a period of at least three weeks, at least 600 mg a week, or
   II. at least about 300 mg daily, taken orally, for a period of at least about 30 days, of
      i. an ester local anesthetic, which may be administered by injection, infusion, or orally, and which is selected from the class consisting of butylaminobenzoate, amydricaine, benoxinate, benzocaine, isobucaine, butacaine, butethamine, meta butethamine, meta butoxycaine, cyclomethycaine, hexylcaine, mepivacaine, meprylcaine, naepaine, parethoxycaine, piperocaine, procaine, 2-chloroprocaine, propanocaine, proparacaine, propoxycaine, tetracaine, tutocaine, the hydrates thereof, the acid salts thereof, and complexes thereof which hydrates, acid salts, and complexes slowly release the active material; or
      ii. metabolic splinters of such ester anesthetic.

2. The method of claim 1 wherein said metabolic splinters are used in said treating.

3. A method of treating depression which method consists essentially of treating a depressed patient with,
   I. by injection or infusion, during a period of at least three weeks, at least 600 mg a week, or
   II. at least about 300 mg daily, taken orally, for a period of at least about 30 days, of
      an ester local anesthetic, which may be administered by injection, infusion, or orally, and which is selected from the class consisting of butylaminobenzoate, amydricaine, benoxinate, benzocaine, isobucaine, butacaine, butethamine, meta butethamine, meta butoxycaine, cyclomethycaine, hexylcaine, mepivacaine, meprylcaine, naepaine, parethoxycaine, piperocaine, procaine, 2-chloroprocaine, propanocaine, proparacaine, propoxycaine, tetracaine, tutocaine, the hydrates thereof, the acid salts thereof, and complexes thereof which hydrates, acid salts, and complexes slowly release the active material.

4. The method of claim 3 wherein said ester anesthetic is procaine, procaine hydrates, procaine acid salts, or procaine complexes, which hydrates, salts and complexes slowly release the procaine.

5. The method of claim 4 wherein said treating is with a mixture of procaine hydrochloride, benzoic acid, dipotassium metabisulfite, and disodium phosphate.

6. The method of claim 5 wheein the relative weight proportions of said recited ingredients are: procaine hydrochloride, 0.1000 g; benzoic acid, 0.0060 g; dipotassium metabisulfite, 0.0050 g; and disodium phosphate, 0.0005 g.

7. The method of claim 6 were said recited ingredients are dissolved in water to make 5 cc of solution.

8. The method of claim 6 where said recited ingredients are admixed with excipients to form a tablet containing the recited amount of each of said recited ingredients.

9. A method of treating depression which method consists essentially of treating a depressed patient with,
   i. an ester local anesthetic, which may be administered by injection, infusion, or orally, and which is selected from the class consisting of butylaminobenzoate, amdyricaine, benoxinate, benzocaine, isobucaine, butacaine, butethamine, meta butethamine, meta butoxycaine, cyclomethycaine, hexylcaine, mepivacaine, meprylcaine, naepaine, parethoxycaine, piperocaine, procaine, 2-chloroprocaine, propanocaine, proparacaine, propoxycaine, tetracaine, tutocaine, the hydrates thereof, the acid salts thereof, and complexes thereof which hydrates, acid salts, and complexes slowly release the active material; or
   ii. metabolic splinters of such ester anesthetic; on a regimen,
      I. of about four weeks, of from about 600 mg per week to less than a toxic amount on a daily basis, by injection or infusion or,
      II. about 300–900 mg daily, taken orally, for at least about four weeks.

10. A method of treating depression which method consists essentially of treating a depressed patient with,
    an ester local anesthetic, which may be administered by injection, infusion, or orally, and which is selected from the class consisting of butylaminobenzoate, amydricaine, benoxinate, benzocaine, isobucaine, butethamine, meta butethamine, meta butoxycane, cyclomethylcaine, hexylcaine, mepivacaine, meprylcaine, naepaine, parethoxycaine, piperocaine, procaine, 2-chloroprocaine, propanocaine, proparacaine, propoxycaine, tetracaine, tutocane, the hydrates thereof, the acid salts thereof, and complexes thereof which hydrates, acid salts, and complexes slowly release the active material,
    I. of about 4 weeks, of from about 600 mg per week to less than a toxic amount on a daily basis, by injection or infusion; or
    II. about 300–900 mg daily, taken orally, for at least about four weeks.

11. The method of claim 10 wherein said maximum daily dosage by injection or infusion is less than 1,000 mg.

12. The method of claim 11 wherein said maximum daily dosage by injection or infusion is not more than 500 mg.

13. The method of claim 10 wherein said regimen (I) may include the first week as an adjustment period wherein the treatment level is not more than 300 mg distributed over that first week.

14. The method of claim 10 wherein said regimen (I) by injection or infusion consists essentially of, for a mildly depressed patient,
    a. a first four week treatment period, as defined;
    b. an off-period of about two weeks; and
    c. a second four week treatment period, as defined; and for a more severely depressed patient additional course or courses consisting of a four week treatment period, as defined, and a two weak off-period are added to aforesaid (a-c) treatment.

15. The method of claim 14 wherein said regimen (I) by injection or infusion may include in each four week treatment period, a first week adjustment period wherein the treatment level is not more than 300 mg distributed over that first week.

16. The method of claim 10 where said treated depressed patient is placed on a maintenance program having about four week treatment periods, by injection or infusion, according to regimen (I) and having about 4-6 week off-periods.

17. The method of claim 10 wherein the regimen (II) by oral ingestion consists essentially of, for a mildly depressed patient,
   a. a first treatment, as defined, of about 30-42 days;
   b. an off-period of about 14 days; and
   c. a second treatment period, as defined, of about 30-42 days; and, for a more severely depressed patient, additional course or courses consisting of an about 30-42 day treatment period, as defined, and an about 14 day off-period are added to aforesaid (a-c) treatment.

18. The method of claim 10 wherein said treated depressed patient is placed on a maintenance program having about 30-42 day oral ingestion treatment periods according to regimen (II), as defined, and having off-periods of about 4-8 weeks.

19. The method of claim 10 wherein said depressed patient has an age of at least about 45 years.

20. The method of claim 10 wherein said treating includes along with said ester anesthetic an organic weak acid, a sulfite salt, and an acid salt.

21. A method of treating depression in a patient having an age of at least about 45 years, which method consists essentially of:
   1. injecting or infusing said patient with three 100 mg portions of ester anesthetic aqueous solution, each portion consisting of procaine hydrochloride, 100 mg; benzoic acid, 6 mg; dipotassium metabisulfite, 5 mg; and disodium phosphate, 0.5 mg, all dissolved in 5 cc of water, distributed over the first week of said treatment;
   2. injecting or infusing said patient in each of the second, third, and fourth weeks of said treatment with a total of 600 mg of procaine hydrochloride in the defined solution of (1), said 600 mg being distributed over each of said weeks.

22. The method of claim 21 wherein in (2) three 200 mg portions, as defined in (1) are injected or infused in each of said weeks.

* * * * *